United States Patent [19]

Wretlind et al.

[11] 4,168,308

[45] Sep. 18, 1979

[54] COMPOSITION FOR ENHANCING THE ADMINISTRATION OF PHARMACOLOGICALLY ACTIVE AGENTS

[75] Inventors: Karl A. J. Wretlind, Stockholm; Stellan Ljungberg, Lidingö; Ivan Håkansson, Huddinge; Bengt M. Ajaxon, Upsala, all of Sweden

[73] Assignee: Apoteksvarucentralen Vitrum AB, Sweden

[21] Appl. No.: 854,404

[22] Filed: Nov. 23, 1977

Related U.S. Application Data

[60] Division of Ser. No. 666,264, Mar. 12, 1976, Pat. No. 4,073,943, which is a continuation-in-part of Ser. No. 504,880, Sep. 11, 1974, abandoned, which is a continuation-in-part of Ser. No. 88,474, Nov. 10, 1970, abandoned, which is a continuation-in-part of Ser. No. 754,738, Aug. 22, 1968, abandoned.

[51] Int. Cl.$^2$ .................... A61K 31/02; A61K 31/33; A61K 31/47; A61K 31/075; A61K 31/135; A61K 31/245; A61K 31/415; A61K 31/515

[52] U.S. Cl. .................... 424/244; 424/254; 424/258; 424/263; 424/273 P; 424/310; 424/330; 424/339; 424/350; 424/358; A61K/31/44

[58] Field of Search ............. 424/358, 254, 244, 263, 424/258, 330, 273, 310, 339, 350

[56] References Cited

U.S. PATENT DOCUMENTS

| 2,303,236 | 11/1942 | Shelton et al. | 424/358 |
|---|---|---|---|
| 2,867,565 | 1/1959 | Feinstone | 424/358 |
| 2,972,565 | 2/1961 | Zilversmit | 424/358 |
| 2,988,484 | 6/1961 | Barsky | 424/358 |
| 3,089,823 | 5/1963 | Czarnecki | 424/358 |
| 3,169,094 | 2/1965 | Wretlind | 424/358 |
| 3,216,897 | 11/1965 | Krantz et al. | 424/358 |
| 3,240,670 | 3/1966 | Feinberg | 424/358 |
| 3,384,545 | 5/1968 | Aiello et al. | 424/358 |

*Primary Examiner*—Stanley J. Friedman
*Attorney, Agent, or Firm*—Zalkind & Shuster

[57] ABSTRACT

According to the invention, the parenteral administration of water-insoluble pharmacologically active agents is enhanced wherein the agents are administered in the lipoid phase of a carrier emulsion comprising a microemulsion of a finely dispersed lipoid in an aqueous phase. The lipoid preferably has a mean particle size below 1 micron. This makes it possible to administer water-insoluble agents in high concentrations, and thus a lower dose, whereby a rapid onset of the pharmacological effect is accompanied by a markedly reduced incidence of injury to body tissues.

8 Claims, No Drawings

COMPOSITION FOR ENHANCING THE ADMINISTRATION OF PHARMACOLOGICALLY ACTIVE AGENTS

This application is a division of application Ser. No. 666,264, filed Mar. 12, 1976, now U.S. Pat. No. 4,073,943, which is in turn a continuation-in-part of application Ser. No. 504,880, filed on Sept. 11, 1974, now abandoned, which is a continuation-in-part of application Ser. No. 88,474, filed on Nov. 10, 1970, which in turn is a continuation-in-part of the application Ser. No. 754,738, filed on Aug. 22, 1968. Application Ser. Nos. 88,474 and 754,738 have now been abandoned.

BACKGROUND OF THE INVENTION

It is now a well established fact that a prerequisite for the action of a drug is its ability to penetrate the lipid cell membranes. A substance can act only through its undissociated, lipid soluble part. This sets a limitation for the intravenous administration of compounds with a $pK_a$ value far from the physiological pH range. On the other hand, a drug has to be dissolved in a physiological vehicle, which normally is an isotonic aqueous solution. Thus, many drugs can only be administered orally as tablets or as suspensions, despite the fact that there is a marked therapeutic need for a parenteral route of administration.

The degree of protein binding differs from drug to drug and from species to species. The albumin bound part of a drug may be regarded as a floating depot, but it has no pharmacological effect per se. Repeated administrations sooner or later give a saturation of the albumin binding capacity and finally enough free drug to give a pharmacological effect.

The physiological mechanism of the fat transport in the blood and lymph is by chylomicrons with a median particle diameter between 0.2 and 0.3 $\mu m$ (range 0.05–0.50 $\mu m$) and containing phospholipids and protein in the membrane.

In the administration of pharmacologically active agents, it has up to now mostly been necessary to use waater-soluble agents or to transform the agents into a water-soluble form, so that a solution can be obtained having the properties required for the administration. The use of the agents in a water-soluble form, however, has often had several disadvantages. For instance, the aqueous solutions may often be acidic or basic, which may cause side effects. Also, it may sometimes by difficult to attain a desired effect, as the solutions cannot be tolerated by the patient.

It has long been postulated that a higher degree of lipophilisity will support an increased pharmacological action of a pharmacon. In 1937 Meyer said that "Narcosis commences when any chemical indifferent substance has attained a certain molar concentration in the lipids of the cell." Until now, it has been difficult to deny or accept this theory as there was no way to administer these lipophilic and hydrophobic substances so that the pharmacokinetics of the compounds could not be investigated.

It is known from Remington's Pharmaceutical Sciences, 13th Edition, 1965, Page 288, Column 2, Line 23, that "Most stable emulsions have particle sizes in the range of 0.25 to 5.0 microns ($\mu$)." However, the reference is to emulsions in general without any appreciation of the utilization of such emulsions for the parenteral administration of oil-soluble pharmacologically active agents, and more specifically there is no appreciation that such emulsions can be utilized as a carrier emulsion to enhance the parenteral administration of oil-soluble pharmacologically active agents whereby a lower dose rate can be utilized than heretofore to achieve a given effect.

U.S. Pat. No. 2,972,565 to Zilversmit discloses fat concentrates for use in the preparation of fat-in-water emulsions when diluted with water and disclosed as suitable for intravenous administration. However, we have made extensive tests in accordance with the examples of the Zilversmit patent, and all tests have ended in failure. Even with the use of modern high-speed emulsifying equipment, it has not been possible to prepare emulsions from Zilversmit's concentrates which have had the small and uniform particle size which is essential in accordance with the present invention. When administering placebo emulsions of this type to mice, up to 50% of the test animals have died. The teachings of the patent to Zilversmit cannot be considered to lead one skilled in the art to the present method of enhancing the parenteral administrations of oil-soluble pharmacologically active agents.

DESCRIPTION OF THE INVENTION

The present invention now refers to a composition for enhancing the administering of water-soluble pharmacologically active agents. According to the invention, a method of administering a pharmacologically active, oil soluble agent having a diagnostic or therapeutic effect is disclosed which comprises the steps of dispersing a pharmacologically acceptable lipoid in a pharmacologically acceptable aqueous solution to form an oil-in-water emulsion for stabilizing the dispersion of the lipoid in the form of particles substantially less than 4 microns in diameter, and generally of a mean particle size not over 1 micron, predominantly dissolving the active agent in the lipoid, and parenterally administering the emulsion with the active agent dissolved in the lipoid phase thereof. Through this method, an enhanced diagnostic or therapeutic effect is achieved with a rapid onset accompanied by a reduced incidence of injury to body tissues.

By the present invention, the disadvantages mentioned in the background of the invention can be avoided, as the active agents are administered dissolved or dispersed in a system of at least one finely dispersed hydrophobic component in at least one hydrophilic component, and primarily then in an emulsion or suspension of a pharmacologically inert fat or oil in an aqueous phase. Also, the agents may be used here without affecting the pH or the osmotic pressure of the aqueous phase, as the agent will mainly be present in a dissolved or disposed state in the hydrophobic phase, and will not have any effect on pH or osmotic pressure. Because of this, the method of administration according to the invention will cause a lower occurrence of injuries to the body tissues. In most cases, the agent also gives a stronger effect and more rapid onset. Unexpectedly, this permits a smaller amount of the agent, i.e. a lower dose, to be used to achieve or maintain an effect that would otherwise require a significantly higher dose.

The aforementioned protein binding will also be reduced, as the agent is not in close contact with the proteins. A longer duration of the effect is also obtained in those cases where the agent normally is attacked rapidly by enzymes in metabolic processes. This is a very important characteristic of the present invention: a rapid onset and a good effect with a longer duration than for the water-soluble salt of the agent. It is a well known fact that the previous use of oil in injections has resulted in a slow release of the active agent from the site of injection in order to protect the patient from side effects due to overdosage. See U.S. Pat. No. 3,240,670 (column 1, line 17).

In the past, it has been the opinion of those skilled in the art that for parenteral injections, especially then intravenous injection only aqueous systems could be used. See, for instance, "Husa's Pharmaceutical Dispensing", Mack Publishing Company, Easton, Pa. (196 However, it has now been shown that provided the necessary precaution are taken, it is not only possible to use the new method of administration by parenteral injection, but even that superior results are attained. In view of the prior art, this is unexpected.

In the use of fat emulsions for intravenous nutrition, a possibility may also be stressed. In accordance with the invention, water-insoluble agents for therpeutic or diagnostic purposes may be administered to the patient simultaneously with the infusion of the fat emulsion.

It may occur that the active agent is not completely dissolved in the hydrophobic phase. It may have a greater affinity to the hydrophobic phase on account of its hydrophobic properties, but depending upon the distribution equilibria, both of the phases may contain the active agent. However, according to the most preferred embodiment, the agent is present predominantly in the hydrophobic phase, in a dissolved state.

The method of the invention comprises most of the administration ways known in the medical art, but is especially intended for parenteral administration, preferably then intravenously, but also intramuscularly or subcutaneously. Examples of administration methods, other than those mentioned above, are the following:
Parenterally:
  intradermally
  intraarterially
  intraspinally
  intrathecally
  intrapleurally
  intraperitoneally
  intrasynovially
Locally The local administration mentioned above is not intended to refer to external local or topical administration, such as an unguent or cream, but rather to an internal local administration, such as directly in an operation wound and the like, where the emulsion with the active agent gets into a direct contact with the blood and lymph vessels.

The active agents with a therapeutic and/or diagnostic effect, which are to be used in the method of the invention, can be of very varying types, and the selection of these agents is only restricted by the conditions that they must be compatible with the vehicle system of several phases and that no harmful side effects may arise. In all cases an agent will be used which is soluble in the hydrophobic phase, such as an oil-soluble agent, but the agents may then also be partly soluble in the hydrophobic phase and be present in it with the other part as an emulsion or suspension on account of their greater affinity to this phase. It is also possible to administer simultaneously oil-soluble and water-soluble agents, each of these primarily being present in the phase to which they have the greatest affinity. However, that condition must always be satisfied that it must always be possible to combine the various components to a stable system with the desired properties, and no harmful side effects must arise.

At room temperature, the active agents are usually solids or liquids with a boiling point above 140° C. in order to avoid transport from the blood system through the capillaries in the lungs. They may also be lower boiling liquids, the salt form of which is solid. In any case, it is necessary that the agents are oil soluble.

Pharmacologically active agents which may be administered in accordance with the present invention, may be selected, but are not limited to the following groups:
Centrally and peripherally acting agents:
  depressants
  anaesthetics
  analgetics
  stimulants
  spasmolytics
  muscle relaxants
  vasodepressants
X-ray contrast agents In addition to the active agent or agents and the hydrophilic component, which consists of an aqueous solution, and the hydrophobic component, which consists of a pharmacologically inert lipoid, the compositions of the invention may contain other substances. These may for instance be preservatives, agents for pH adjustment, and agents for adjustment of the osmotic pressure. One of the most important additives will consist of one or more agents for achieving a stable dispersion of the hydrophobic phase in the hydrophilic phase. Many emulsifiers and suspension agents of a natural as well as synthetic origin may be used.

The preparations according to the method of the invention may contain from 1 up to 10 hydrophilic components, and usually they contain about 5 hydrophilic components.

As has been indicated above, the carrier or vehicle for the preparations according to the invention consists of a system of at least one hydrophobic component finely dispersed in at least one hydrophilic component. In most cases, the vehicle will consist of an emulsion or suspension of a fat or an oil in an aqueous solution, both phases of course being pharmacologically acceptable. For this certain conditions must be fulfilled. In a finely dispersed system which is to be introduced into the blood vessels, all the particles must have a diameter below 4 microns, as they will otherwise get stuck in the capillary vessels. A particle size of 1 micron or less is a salient aspect, and this also makes the system more stable. Moreover, the system must also be of such a type that the particles do not form aggregates. Furthermore, the vehicle system must also be able to withstand autoclaving and preferably also freezing, and it must have such a composition and such properties that it can be stored for a long time without physical and chemical breakdown. It is of course also an important requirement that the vehicle system itself must not cause undesirable effects.

In the vehicle systems most commonly used, which consist of an emuslion or suspension of a pharmacologically inert oil or fat in an aqueous solution, the hydrophobic component usually consists of a fat or an oil of vegetable or animal origin, such as soybean oil, cottonseed oil, coconut oil or olive oil. In order to obtain a stable system, it is furthermore necessary to include stabilizers of a natural or synthetic origin, such as phosphatides, polypropylene glycol, polyethylene glycol, polyglycerol monooleate, etc. The emulsions or suspensions used usually have a fat content of 0.1–99 percent by weight, depending on the form of application. The amount of stabilizer in the compositions is determined by the properties of the system and depends on the nature of the dissolved active agent and usually lies between 0.1 and 20 weight percent.

For the purpose of the invention, suitable fat emulsions have been prepared, and one example of such emulsions is described in the U.S. Pat. No. 3,169,094. This emulsion consists of soybean oil in water with native egg phosphatides added as a stabilizer, and it has proved to be free from harmful side effects also when administered in such large quantities as are required in intravenous fat nutrition. Other oils or fats and other stabilizers may also be used for the purpose of the invention, even if they give side effects when used for intravenous nutrition, as they are administered in much smaller quantities when used as vehicles for pharmaceutically active agents.

The invention is further illustrated by the following examples, which, however, are not limitative.

EXAMPLE 1

5 g of phenyramidol base is dissolved in 95 g of soybean oil. An emulsion is prepared of 20 g of such a soybean oil solution, 1 g of egg phosphatides, 2.5 g of glycerol and 0.5 g of Myrj 52 (a registered trade mark for a nonionic emulsifier consisting of a polyoxyethylene derivative of fatty acids, from Atlas Co, described on page 709 of the Merck Index, 8th Ed., and on page 389 of the Extra Pharmacopoeia, Martindale, 26th Ed.), and sterile water to 100 ml. In the preparation, the conventional precautions for the preparation of bacteriologically acceptable injection solutions must be observed.

In pharmacological testing on mice, this composition shows a better effect than an aqueous solution of phenyramidol hydrochloride. Furthermore, the aqueous solution also has a lower pH value.

EXAMPLE 2

3.75 g hexobarbital
10 g soybean oil
25 g ethanol
1 g egg phosphatides
0.5 g Myrj 52 (same product as in Example 1)
Sterile water to 100 ml An emulsion with the above composition is prepared in the same manner as in Example 1. In the finished emulsion, the majority of the particles have a size below 1 micron.

EXAMPLE 3

Mecamylamine (3-methylaminoisocamphane hydrochloride) is a ganglion-blocking secondary amine, and as a base, it is an oily liquid which is soluble in lipids. Its toxicity ($LD_{50}$) after intravenous administration has been estimated in male albino mice of the NMRI strain in accordance with the method of the Nordic Pharmacopoeia. The following preparations were used:

Mecamylamine hydrochloride, 1% dissolved in saline
Mecamylamine base, dissolved in soybean oil and emulsified in the conventional way. Final concentration 1%.

Mecamylamine base, directly emulsified in 5.5% glucose solution with the aid of Pluronic F-68 (a registered trade mark for a nonionic emulsifier consisting of a block polymer of ethylene oxide and propylene oxide, from Wyandotte Chemical Corporation, described on page 392 of the Extra Pharmacopoeia, Martindale, 26th Edition) and an ultrasonic apparatus (20.000 Hz). Final concentration 1%.

The injections were given in the dorsal tail vein at a speed of 0.1 ml per 5 seconds. The results are listed in Table 1.

TABLE I:

| Intravenous toxicity of different mecamylamine preparations in mice. | | |
|---|---|---|
| Preparation | $LD_{50}$[1] mg/kg | Survival time sec. ± S.E. |
| Mecamylamine HCl | 16.3 (15.5–17.6) | 55 ± 5.1 |
| Mecamylamine in oil[2] emulsion (Intralipid) | 15.4 (14.8–16.1) | 52 ± 3.1 |
| Mecamylamine in water emulsion | 11.9 (11.4–12.4) | 56 ± 3.8 |

[1]Fiducial limits at P = 0.05
[2]"Intralipid" is a registered trade mark for a fat emulsion for intravenous nutrition. It is described in U.S. Pat. No. 3,169,094.

The intravenous toxicity of mecamylamine hydrochloride has earlier been found to be, by Stone et al.: 21.0 mg/kg [Stone, C. Torchiana, M. L., Navarro, A. and Beyer, K. H.: "Ganglionic block properties of 2-methylaminoisocamphane hydrochloride (Mecamylamine) a secondary amine", J. Pharmacol. Exptl. Therap.: 117: 169–183 (1956)] and by Corne & Edge: 12.9 mg/kg [Corne, S. J. and Edge, N. D.: "Pharmacological properties of pempidine (1,2,2,6,6-pentamethylpiperidine, a new ganglio-blocking compound", Brit. J. Pharmacol.: 13: 339–349 (1958)], which statistically does not differ from the above results.

All the quantal log-dose-response lines had the same slope and a comparison between the hydrochloride and the two emulsions showed a slight increase in toxicity for the pure base preparation, 138% (125–150%), but no difference for the soybean oil preparation, 106% (99–113%), the fiducial limits given at P=0.05.

As can be seen from the table, there was no difference in survival time (the time from the injections to death) between the preparations.

To summarize, it can be stated that the toxic effects of mecamylamine have not been altered to any notable degree by the different galenic modifications used.

EXAMPLE 4

The question to be considered here is the influence of protein binding on a drug, which is dissolved in the oil phase of an emulsion. Quinidine is bound to plasma albumin to an extent of about 80%, and the therapeutic use of its water soluble salts by intravenous injection may therefore be hazardous. The individual rate and speed of albumin binding seems to be more important than the magnitude of the dose given.

A male mongrel dog with an irregular heart rate, between 60 and 130 beats per minute, was anaesthesized with urethane, and blood pressure, ventilation, heart rate and ECG were recorded.

Quinidine base, dissolved in soybean oil and suspended in water with a final concentration of 0.3% was injected into the femoral vein (1 mg/kg). A few seconds after the injection was finished, the heart rate was regulated, and this effect persisted for about 30 minutes.

When a placebo emulsion was administered, no effect could be registered, but when the quinidine injection was repeated, there was again a regulation, which persisted for about one hour.

These results have been followed up in strophantine induced arrythmias in dogs, and it is found that quinidine base dissolved in oil and emulsified in water is a better and safer preparation for intravenous injections than aqueous solutions of the quinidine salts.

EXAMPLE 5

Hexobarbital 1%

Hexobarbital—1%
Phospholipids—0.5%
Span 80[1]—0.05%
Oleic acid—2.5%
Soybean oil—17.5%
Glycerol—2.5%
Tween 80[2]—0.05%
Sterile water to 100%

[1] Span 80 is a registered trade mark for an emulsifier, consisting of sorbitan esters of long chain fatty acids; page 973, The Merck Index, Eighth Edition, 1968
[2] Tween 80 is a registered trade mark for an emulsifier, consisting of polyoxyethylene sorbitan monooleate; page 973, The Merck Index, 8th Ed., 1968

The emulsion has an instant action when administered intravenously.

Rats:

At a dose of 60 mg/kg, the animals fall asleep without excitation. A constant supply of 35 mg/kg gives continuous sleep and after interruption of the infusion, the animals wake up after about 3 minutes.

Cats:

The effects of the emulsion on the blood pressure when given intravenously in a dose of 5-10 mg/kg was registered on a chloralose-anaesthetized cat. The emulsion and a solution of sodium hexobarbital both gave a depression of about 60 mm Hg with about the same duration.

Mouse:

The sleeping time after a single dose injection of the emulsion was shorter than the sleeping time after injection of an aqueous solution of sodium hexobarbital:

| Dose | Sleeping time | |
|---|---|---|
| | emulsion | sodium salt |
| 72 mg/kg | 130 sec. | 172 sec. |
| 86 mg/kg | 583 sec. | 905 sec. |

In accordance with common practice, the sleeping time has been set as the duration of the loss of the righting reflex.

EXAMPLE 6

Chloralose 0.5%

Chloralose—0.5%
Soybean oil—10%
Monoglycid 18/98—10%
Pluronic F-68—0.5%
Glycerol—2.5%
Sterile water to 100%

In rats, an instant sleeping effect was obtained.

EXAMPLE 7

Tribromoethanol 2%

Tribromoethanol—2%
Soybean oil—10%
Span 80—0.14%
Tween 80—0.36%
Phospholipids—0.5%
Glycerol—2.5%
Sterile water to 100%

In rabbits, 80 mg/kg, administered intravenously slowly (5 minutes) gives a light sleep with an onset time of 30 seconds and a duration of 9 minutes. The awakening was without remarks.

The following preparations have also been prepared and administered by parenteral injection with good results:

EXAMPLE 8

Pentazocine

Pentazocine—0.05 g
Soybean oil—10 g
Pluronic F-68—0.5 g
Glycerol—2.5%
Sterile water to 100 ml

EXAMPLE 9

Phenylbutazone

Phenylbutazone—2 g
Soybean oil—10 g
Acetylated monoglycerides—10 g
Glycerol—2.5 g
Pluronic F-68—0.5%
Sterile water to 100 ml

EXAMPLE 10

Cyclandelate

Cyclandelate—0.2 g
Soybean oil—15 g
Phosphatides—0.5 g
Pluronic F-68—0.5 g
Glycerol—2.5 g
Sterile water to 100 ml Cyclandelate (3,5,5-trimethylcyclohexyl mandelate) which is almost completely insoluble in water has been administered intraarterially in the hind leg of cats anaesthetized with chloralose, and in doses of about 1-2 mg/kg body weight, causing a marked vasodilatation within a few seconds, especially in noradrenaline induced vasoconstriction. The systemic effect (heart rate, blood pressure, etc.) on the circulation of the cats was negligible within the dose range used. It has not been possible earlier to demonstrate this marked local vasodilating effect, as it has not been possible earlier to administer cyclandelate by injection.

EXAMPLE 11

Benzocaine

Benzocaine—2 g
Soybean oil—10 g
Monoglyceride—10 g
Glycerol—2.5 g
Span 65—0.5 g
Sterile water to 100 ml

EXAMPLE 12

Secobarbital

Secobarbital—1.5 g
Soybean oil—15 g
Monoglyceride—5 g
Glycerol—2.5 g
Sterile water to 100 ml

EXAMPLE 13

Quatacaine
Quatacaine—0.5 g
Soybean oil—20 g
Pluronic F-108—1 g
Glycerol—2.5 g
Sterile water to 100 ml

EXAMPLE 14

Lidocaine
Lidocaine—2 g
Soybean oil—15 g
Myvacet 9-40—5 g
Pluronic F-103—1 g
Glycerol—2.5 g
Sterile water to 100 ml "Myvacet 9-40" is a registered trade mark for acetylated monoglycerides, sold by Distillation Products Co.

EXAMPLE 15

Thiopental
Thiopental—0.75 g
Soybean oil—20 g
Myvacet 9-40—7.5 g
Pluronic L-81—1 g
Glycerol—2.5 g
Sterile water to 100 ml

EXAMPLE 16

Pentobarbital
Pentobarbital—0.75 g
Soybean oil—20 g
Myvacet 9-40—7.5 g
Pluronic F-88—1 g
Glycerol—2.5 g
Sterile water to 100 ml

EXAMPLE 17

In this example, the acute toxicity ($LD_{50}$) aand the anticonvulsant acitivity of various diazepam formulations has been investigated in mice. In accordance with the invention, diazepam emulsion was prepared with the following composition:

Diazepam (WHO)—0.5 g
Soybean oil—15.0 g
Acetylated monoglycerides—5.0 g
Egg yolk phosphatides—1.2 g
Glycerol—2.5 g
Distilled water to 100.0 ml This formulation was compared to a commercial diazepam formulation for injection, which is sold under the registered trade mark Valium from Hoffmann La Roche & Co. This commercial diazepam formulation contains 5 mg/ml of diazepam dissolved in an aqueous mixture containing 41.4% propylene glycol, 8.06% ethanol, 1.57% benzyl alcohol, 0.12% benzoic acid and 4.88% sodium benzoate. It is necessary to use this mixture, as diazepam is not soluble in water alone.

The test results showed that the two formulations had nearly equal anticonvulsant activities, but that the diazepam formulation of the invention had an $LD_{50}$ of 283.3 mg/kg, while the $LD_{50}$ of the commercial diazepam formulation was 83.4 mg/kg. It is believed that the solvents necessary in the commercial diazepam formulation contribute in a large degree to its greater toxicity, and this has been confirmed in a test with a placebo solution using only the solvents of the commercial diazepam formulation. This placebo solution had an $LD_{50}$ of 90.5 mg/kg.

Thus, it has been shown that the administration in accordance with the invention can be made much safer than in prior methods.

EXAMPLE 18

This example shows how the incidence of injuries in the form of thromobphlebitis is drastically reduced through the present invention. Thromobphlebites are inflammations in the venous walls, and they can sometimes have quite serious consequences. At intravenous injections, however, they have been such a common occurrence that their appearance has sometimes not even been noted, but they have been considered as an unavoidable evil. In the use of barbiturates for intravenous anaesthesia, the rate of thrombophlebitis within two weeks after injection has been found to be from 10 to 30 percent.

In a comparative test, a commercial 5.5% water solution of Narkotal, trade mark for pronarcon or 5-(2-bromoallyl)-5-isopropyl-1-methylbarbituric acid, was administered intravenously to 53 patients. It was found that within a week, 16 of the patients, i.e. 30%, developed symptoms of thrombophlebitis. In another test, an emulsion prepared in accordance with the invention and containing 1.5 percent secobarbital in the oil phase was administered intravenously in the same way to 62 patients. It was found that none of these patients developed any thrombophlebitis symptoms. This clearly shows that the risk of injuries to the tissues is markedly decreased in the method of the invention.

EXAMPLE 19

This example shows that it is preferred that theactive agent used has a boiling point above 140° C.

An emulsion composition was prepared containing 5 percent of methoxyflurane (2,2-dichloro-1,1-difluoro-ethyl methyl ether; b.p. 105° C.) in a carrier system of soybean oil emulsified in water with the help of egg phosphatides. This formulation was administered to mice, and the $LD_{50}$ value was found to be 150.4 mg/kg.

It was not possible to establish a relation between the sleeping time and the administered dose. Within a dose range from 118 to 190 mg/kg, the surviving animals slept from 0.6 to 2.0 minutes. There was, however, no correlation between the magnitude of the dose and the sleeping time, and therefore, this cannot be considered as a genuine effect. The reason for this is that the methoxyflurane was eliminated through the respiratory tract so quickly that the pharmacological effect was not obtained.

As discussed, a salient aspect of the invention resides in the fact that the mean particle size of the lipid particles comprising the inner phase of the carrier emulsion utilized in carrying forth the present method is preferably not over 1 mm. To facilitate the practice of the present invention the following method is discussed as being suitable for the determination of the particle size distribution.

A convenient method to determine the size distribution pattern in particulate formulations has been published by Groves, Yalabik and Tempel Powder Technology 11, 245–255, 1975. Its application in lipid emulsion formulations was described by Groves and Yalabik Powder Technology, presently in press. The method uses a laser beam and photodetector as the sensing system for the lipid particles in a centrifugal field and the size distribution is calculated by using the centrifugal analogue of Stokes' law.

The laser photosedimentometer was used to determine the particle size distribution of seven different emulsions of types according to the present invention. The factor $d_{st(50)}$ (Stokes' diameter) is calculated in the particle size determinations. This value indicates the mean diameter (at 50%) and the width of the distribution is expressed by the slope (standard deviation) in TABLE II.

TABLE II:

| Emulsion type | Stokes' diameter $d_{st(50)}$ in um | Slope |
|---|---|---|
| (1) Fat emulsion 10% | 0.15 | 1.42 |
| (2) Fat emulsion 20% | 0.23 | 1.56 |
| (3) Fat emulsion 50% | 0.50 | 1.40 |
| (4) Emulsion with Soy bean + Pluronic F 108 | 0.13 | 2.43 |
| (5) Emulsion with Soy bean oil + Pluronic F 68 | 0.63 | 1.43 |
| (6) Diazepam emulsion | 0.19 | 1.41 |
| (7) Placebo emulsion to diazepam | 0.25 | 1.52 |

While it is believed that the unexpected result obtained by the practice of the method of the present invention is apparent from the foregoing specific Examples, particular attention is directed to, for instance, the enhanced administration of the pharmacological agents diazepam and barbituates, see Examples 17 and respectively.

From a consideration of Example 17 it will be seen that the acute toxicity of diazepam when administered parenterally in accordance with the present invention is substantially lower than than of diazepam administered by a prior parenteral method. In Example 18 it will be seen that the use of barbituates for intravenous anaesthes administered parenterally in accordance with the present method result in a marked decrease of risk of injury to tissues, namely inflammation of the venous walls thereby greatly enhancing the administration of barbituates for intravenous anaesthesia.

We claim:

1. A composition for enhancing parenteral administration comprising a stable, oil-in-water emulsion containing a pharmacologically inert lipoid as a hydrophobic phase dispersed in a hydrophilic phase and an effective dose of a pharmacologically active, oil-soluble agent predominantly dissolved in said lipoid at a fraction ratio thereto in the hydrophobic phase, said lipoid being dispersed in the emulsion as finely divided particles having a mean particle size less than 1 micron to achieve rapid onset of an acceptable therapeutic effect attributable to said effective dose of the active agent, said active agent being selected from a class of substances consisting of central depressants, analgesics, spasmolytics, muscle relaxants and vasodepressants.

2. A composition as defined in claim 1, wherein the oil-soluble pharmacological agent is a central depressant from a class of compounds consisting of: hexobarbital, secobarbital, thiopental, pentobarbital and diazepam.

3. A composition as defined in claim 1, wherein the oil-soluble pharmacological agent is an anaesthetic from a class of compounds consisting of: hexylether, tribromoethanol and halothane.

4. A composition as defined in claim 1, wherein the oil-soluble pharmacological agent is an analgesic from a class of compounds consisting of: pentazocine, phenylbutazone, benzocaine, quatacaine and lidocaine.

5. A composition as defined in claim 1, wherein the oil-soluble pharmacological agent is a spasmolytic from a class of compounds consisting of: mecamylamine and cyclandelate.

6. A composition as defined in claim 1, wherein the oil-soluble pharmacological agent is a vasodepressant from a class of compounds consisting of: quinidine and cyclandelate.

7. A composition as defined in claim 1, wherein the oil-soluble pharmacological agent is a muscle relaxant from the compounds of phenyramidol.

8. A composition for enhancing parenteral administration comprising a stable, oil-in-water emulsion containing a pharmacologically inert lipoid as a hydrophobic phase dispersed in a hydrophilic phase and an effective dose of a pharmacologically active, oil-soluble agent predominantly dissolved in said lipoid at a fraction ratio thereto in the hydrophobic phase, said lipoid being dispersed in the emulsion as finely divided particles having a mean particle size less than 1 micron to achieve rapid onset of an acceptable therapeutic effect attributable to said effective dose of the active agent, said active agent being selected from a class of substances consisting of: phenyramidol, hexobarbital, mecamylamine, quinidine, chloroalose, tribromoethanol, pentazocine, phenylbutazone, cyclandelate, benzocaine, secobarbital, quatacaine, lidocaine, thiopental, pentobarbital, diazepam, and methoxyflurane.

* * * * *